United States Patent [19]

Scheer et al.

[11] Patent Number: 5,118,619
[45] Date of Patent: Jun. 2, 1992

[54] METHOD FOR THE FERMENTATIVE PRODUCTION OF L-ISOLEUCINE FROM D,L-α-HYDROXYBUTYRATE

[75] Inventors: Elisabeth Scheer, Aachen; Hermann Sahm; Lothar Eggeling, both of Jülich; Manfred Kircher, Bielefeld; Wolfgang Leuchtenberger, Bruchkobel, all of Fed. Rep. of Germany

[73] Assignee: Degussa Aktiengesellschaft, Fed. Rep. of Germany

[21] Appl. No.: 59,438

[22] Filed: Jun. 8, 1987

[30] Foreign Application Priority Data

Jun. 6, 1986 [DE] Fed. Rep. of Germany ......... 3619111

[51] Int. Cl.⁵ .................. C12P 13/06; C12P 13/08; C12N 1/20
[52] U.S. Cl. .................. 435/116; 435/115; 435/252.1; 435/843; 435/840

[58] Field of Search ............ 435/116, 115, 252.1, 435/843, 840

[56] References Cited

U.S. PATENT DOCUMENTS 4,411,991 10/1983 Hirakawa et al. .............. 435/115

FOREIGN PATENT DOCUMENTS 29789 11/1968 Japan .

OTHER PUBLICATIONS

Matsushima et al, "Screening of microogranisms for production of L-isoleucine from DL-α-hydroxybutyric acid . . . " Chemical Abstracts vol. 79, 1973 p. 303, 103605m.

Primary Examiner—Irene Marx
Attorney, Agent, or Firm—Cushman, Darby & Cushman

[57] ABSTRACT

A method for the fermentative production of L-isoleucine from D,L-α-hydroxybutyrate by means of mutants of the genus Corynbecaterium which utilize D-lactate.

6 Claims, No Drawings

METHOD FOR THE FERMENTATIVE PRODUCTION OF L-ISOLEUCINE FROM D,L-α-HYDROXYBUTYRATE

The invention relates to a method for the fermentative production of L-isoleucine from the racemic mixture of D- and L-α-hydroxybutyrate by means of mutants of the genus Corynebacterium or Brevibacterium which utilize D-lactate.

BACKGROUND OF THE INVENTION

The amino acid L-isoleucine is essential for man and animal and is widely used as a component of various nutrient mixtures intended for medicinal purposes. Moreover, L-isoleucine is used as an addition for human nourishment and as animal food as well as a reagent for the pharmaceutical and chemical industries.

It is known that L-isoleucine can be fermentatively produced from various carbohydrates such as glucose, fructose, starch hydrolysate, cellulose hydrolysate and molasses or hydrocarbons such as n-paraffins from various precursors of the L-isoleucine biosynthesis. Mainly, members of the genus Corynebacterium, Brevibacterium or Arthrobacter are used for this purpose. They are used in a nutrient solution containing a precursor as well as a carbon and energy source, a nitrogen source, vitamins and other components and which partially convert the precursors to L-isoleucine and accumulate them in the nutrient solution. Threonine, α-aminobutyrate, α-hydroxybutyrate or α-ketobutyrate are used as precursors. These precursors (with the exception of α-ketobutyrate) can each be present in the L and the D form as well as racemate. The precursors are readily accessible in the form of their racemate, so that the complete utilization of the D and L form must be given for an effective use of precursors.

A maximum L-isoleucine concentration of 15.8 g/l was able to be achieved with Brevibacterium thiogenitalis using 30 g/l hydroxybutyrate as precursor (see U.S. Pat. No. 4,329,427).

This method has the disadvantage that hydroxybutyrate is converted in a small yield to L-isoleucine. However, it is not known to what extent the hydroxybutyrate functioned as precursor and whether the D-component of the racemate of hydroxybutyrate is also utilized.

When D, L-α-hydroxybutyrate was used as precursor, it was possible to obtain a yield of 78% with Corynebacterium glutamicum ATCC 21193, but only a maximum L-isoleucine concentration of 7.8 g/l (DE-OS 1,910,428).

Even smaller yields can be achieved with the microorganisms of various genera such as, e.g., Corynebacterium, Brevibacterium, Arthrobacter, etc. described in Published German Application DE-OS 1,912,819 (which is equivalent to U.S. Pat. No. 3,671,396).

The small yields are also caused, among other reasons, by the fact that the microorganisms do not utilize the D-α-hydroxybutyrate.

SUMMARY OF THE INVENTION

The object of the present invention is to provide a method for the fermentative production of isoleucine from D,L-α-hydroxybutyrate in which L-isoleucine can be obtained from the racemate in high concentration with good yields.

According to the invention a method is provided for producing L-isoleucine from D,L-α-hydroxybutyrate by culturing a microorganism of the genus Corynebacterium or Brevibacterium under aerobic conditions in an aqueous culture medium which contains assimilatable sources for carbon and nitrogen and inorganic salts and by isolating the L-isoleucine accumulated in the medium, characterized in that the microorganism used is Corynebacterium or Brevibacterium which was cultured on a solid growth medium with a D-lactate content of 0.1 to 40 mg/ml, preferably 5 to 12 mg/ml.

DETAILED DESCRIPTION OF PREFERRED EMBODIMENTS

The conditions for carrying out the invention occur, for example, on nutrient agar plates of the following composition when maintained at 30° C. for 3 to 10 days:
10 g/l ammonium sulfate, 5 g/l urea, 1 g/l potassium hydrogen phosphate, 0.25 g/l magnesium sulfate, 0.01 g/l iron sulfate,
0.01 g/l calcium chloride, 0.0001 g/l biotin, 10 g/l D-lactate, 15 g/l agar-agar, pH 7.

It is advantageous to select mutants of known Corynebacterium strains for culture which are obtained by UV radiation or by treatment with mutagens such as, e.g., ethyl methane sulfonate, N-methyl-N'-nitro-N-nitrosoguanidine.

A Corynebacterium glutamicum with a D-lactate dehydrogenase activity of 0.05–8 U/mg can be used. Particularly suitable are mutants of Corynebacterium glutamicum ATCC 13032 and ATCC 14310 which were obtained by the known treatment of the last-named strains with N-methyl-N'-nitro-N-nitrosoguanidine and are deposited with the German Strain Collection for Microorganisms in Gottingen under the numbers DSM 3717 and 3718. They grow on the nutrient medium containing D-lactate and contain a D-lactate dehydrogenase activity of approximately 0.25 or 0.4 U/mg while the initial strains contain only approximately 0.1 U/mg.

(The activity was determined in accordance with the procedure described in "Microbiological Reviews" 44; 1980; pp. 106 to 139.) Mutants with a D-lactate dehydrogenase activity of >0.1 to 1.5 U/mg are suitable for the method of the invention.

The fermentation of the isolated mutants of Corynebacterium glutamicum is performed in shake cultures or in fermenters under aerobic conditions at a reaction temperature of 20°–45° C. and a pH of 5–9. Calcium carbonates and ammonium salts are suitable for the correction of the pH. The fermentation medium contains a carbon source, D,L-α-hydroxybutyric acid, a nitrogen source and other elements. Suitable carbon sources for the fermentation are sugar, protein hydrolysates and proteins. D,L-α-hydroxybutyrate can be added to the reaction batch as a free acid or as a salt (such as, e.g., sodium salt or calcium salt) in a concentration of 0.01–50 g/l.

It is preferable if the concentration of the initial compound does not exceed 20 to 40 g/l.

In order to nevertheless achieve a better accumulation of L-isoleucine in the fermentation broth, the D,L-α-hydroxybutyrate is added in portions, taking into consideration the aforementioned preferred maximum values, until the fermentation medium contains 15 to 30 g/l L-isoleucine.

Examples of suitable nitrogen sources are ureas, ammonium salts of organic acids (e.g. ammonium acetate) or ammonium salts of inorganic acids (e.g. ammonium sulfates or ammonium nitrates).

The amount of the carbon sources and nitrogen sources can vary from 0.001–40 g/l. Organic nutrients (such as corn steep liquor, peptone, yeast extract) and/or inorganic constituents (such as potassium phosphate, magnesium sulfate, vitamins such as biotin, and amino acids such as leucine or valine) can also be added to the nutrient solution. The fermentation is performed for 24 to 192 hours, during which L-isoleucine accumulates in the nutrient solution.

In a preferred embodiment D,L or L-leucine is added to the fermentation medium in amounts ranging from 100 to 250 µg/ml, especially 200 µg/ml. This clearly improves the yield of L-isoleucine.

The leucine remains intact, since it obviously has only a regulatory function.

After the fermentation is over, the L-isoleucine is isolated and purified by known methods.

EXAMPLE 1

100 ml of a nutrient solution of the following composition were placed in a 500 ml Erlenmeyer flask with 2 baffles:

40 g/l glucose $\times H_2O$
18 g/l D,L-α-hydroxybutyric acid
20 g/l $(NH_4)_2SO_4$
0.5 g/l $K_2HPO_4$
0.25 g/l $MgSO_4 \times 7H_2O$
0.01 g/l $FeSO_4 \times 7H_2O$
0.01 g/l $MnSO_4 \times 4H_2O$
0.4 mg/l biotin
20 g/l $CaCO_3$
200 mg/l L-leucine Glucose and the neutralized D,L-α-hydroxybutyric acid were separately sterilized, $CaCO_3$, sterilized dry (8 hrs at 150° C.) and added under sterile conditions to the nutrient solution.

5 ml of a 16 hour-old preculture of Corynebacterium glutamicum with elevated D-lactate dehydrogenase activity (DSM 3718), grown in 100 ml complex medium (20 g/l glucose, 10 g/l peptone, 10 g/l yeast extract, 2.5 g/l NaCl, pH 7.4) in a 500 ml Erlenmeyer flask with 2 baffles at 30° C. and 130 rpms served as inoculum of the main culture, which was incubated at 30° C. and 130 rpms. After an incubation time of 72 hours, the fermentation medium contained 14.3 g/l L-Isoleucine. The fermentation medium of the reference batch without D,L-α-hydroxybutyric acid contained no L-Isoleucine.

EXAMPLE 2

The procedure of example 1 was employed; however, the nutrient solution contained 24 g/l D,L-α-hydroxybutyric acid. After a culture time of 72 hours, the fermentation medium contained 16.1 g/l L-isoleucine.

EXAMPLE 3

The procedure of example 1 was employed; however, the nutrient solution contained 400 mg/l L-leucine. After the fermentation, only 6 g/l L-isoleucine could be found.

What is claimed is:

1. In a method for the production of L-isoleucine from D,L-α-hydroxybutyrate by means of culturing a microorganism of the genus Corynebacterium or Brevibacterium under aerobic conditions in an aqueous culture medium which contains assimilatable sources of carbon and nitrogen and inorganic salts and by isolating the L-isoleucine accumulated in the medium, the improvement in which the microorganism used is Corynebacterium or Brevibacterium which was cultured on a solid growth medium with a D-lactate content of 0.1 to 40 mg/ml.

2. A method according to claim 1 in which Corynebacterium glutamicum with a D-lactate dehydrogenase activity of 0.05–8 U/mg is used.

3. A method according to claim 1 or claim 2, in which Corynebacterium glutamicum DSM 3717 or DSM 3718 is used.

4. A method according to claim 1 or claim 2 in which 100 to 250 µg/ml DL- or L- leucine is added to the fermentation broth.

5. A method according to claim 1 or claim 2 in which the concentration of the D,L-α-hydroxybutyrate is maintained below 20 to 40 g/l.

6. Mutants of Corynebacterium glutamicum ATCC 13032 and ATCC 14310 with elevated D-lactate dehydrogenase activity, deposited under numbers DSM 3717 and 3718.

* * * * *

UNITED STATES PATENT AND TRADEMARK OFFICE
CERTIFICATE OF CORRECTION

PATENT NO. : 5,118,619
DATED : June 2, 1992
INVENTOR(S) : Scheer et al

It is certified that error appears in the above-indentified patent and that said Letters Patent is hereby corrected as shown below:

On the title page, item [30] the Foreign Application Priority Data "361911" should read --3619111--.

Signed and Sealed this

Twenty-first Day of December, 1993

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,118,619

DATED : June 2, 1992

INVENTOR(S) : Elisabeth Scheer, Hermann Sahm, Lothar Eggeling, Manfred Kircher, Wolfgang Leuchtenberger It is certified that error appears in the above-identified patent and that said Letters Patent is hereby corrected as shown below:

On the Title Page,

Please change
"[73] Assignee: Degussa Aktiengesellschaft, Fed. Rep. of Germany" to --[73] Assignee: Degussa Aktiengesellschaft and Kernforschungsanlage Julich, both of Fed. Rep. of Germany--

Signed and Sealed this

Twenty-first Day of June, 1994

Attest:

BRUCE LEHMAN

*Attesting Officer*   *Commissioner of Patents and Trademarks*